(12) United States Patent
Gray

(10) Patent No.: US 11,118,218 B2
(45) Date of Patent: Sep. 14, 2021

(54) COMMON PORT EMULSION GENERATION SYSTEM

(71) Applicant: Cypho, Inc., Long Beach, CA (US)

(72) Inventor: Mark A. Gray, Long Beach, CA (US)

(73) Assignee: Cypho, Inc., Avalon, CA (US)

( * ) Notice: Subject to any disclaimer, the term of this patent is extended or adjusted under 35 U.S.C. 154(b) by 1278 days.

(21) Appl. No.: 14/889,132

(22) PCT Filed: Dec. 9, 2013

(86) PCT No.: PCT/US2013/073957
§ 371 (c)(1),
(2) Date: Nov. 4, 2015

(87) PCT Pub. No.: WO2014/089579
PCT Pub. Date: Jun. 12, 2014

(65) Prior Publication Data
US 2016/0167053 A1   Jun. 16, 2016

Related U.S. Application Data

(63) Continuation-in-part of application No. 14/024,145, filed on Sep. 11, 2013, now abandoned.

(60) Provisional application No. 61/700,241, filed on Sep. 12, 2012, provisional application No. 61/734,952, filed on Dec. 7, 2012.

(51) Int. Cl.
*C12Q 1/68* (2018.01)
*C12Q 1/686* (2018.01)
(Continued)

(52) U.S. Cl.
CPC ............ *C12Q 1/686* (2013.01); *B01F 3/0807* (2013.01); *B01F 13/0062* (2013.01);
(Continued)

(58) Field of Classification Search
CPC ....................................................... C12Q 1/68
(Continued)

(56) References Cited

U.S. PATENT DOCUMENTS 5,061,741 A   10/1991   Miyata et al.
7,985,058 B2   7/2011   Gray
(Continued)

FOREIGN PATENT DOCUMENTS

GB         2453585 A  *  4/2009  ............... G01N 1/14
WO    WO 2005/073410 A2    8/2005
(Continued)

OTHER PUBLICATIONS

International preliminary report on patentability dated Jun. 18, 2015 for PCT/US2013/073957.
(Continued)

*Primary Examiner* — Aaron A Priest
(74) *Attorney, Agent, or Firm* — Acuity IP, LLC; Nathan S. Cassell

(57) ABSTRACT

An article for forming emulsion droplets includes a body having an inlet port, an outlet, and a reservoir configured to receive both an aqueous phase and an organic phase through the inlet port. By applying a force to the contents of the reservoir, an aqueous phase stream and a separate organic phase stream from the reservoir are generated and later combined to form emulsion droplets which are dispensed through the outlet, typically into a receptacle for analysis or further processing.

37 Claims, 13 Drawing Sheets

(51) Int. Cl.
  *B01F 13/00* (2006.01)
  *C12Q 1/6844* (2018.01)
  *B01F 3/08* (2006.01)
  *B01L 3/00* (2006.01)
  *B01L 3/02* (2006.01)

(52) U.S. Cl.
  CPC .......... *B01L 3/5025* (2013.01); *C12Q 1/6844* (2013.01); *B01L 3/0241* (2013.01); *B01L 3/50851* (2013.01); *B01L 2200/0673* (2013.01); *B01L 2300/0609* (2013.01); *B01L 2300/0829* (2013.01); *B01L 2300/0867* (2013.01); *B01L 2400/0409* (2013.01)

(58) Field of Classification Search
  USPC .......................................................... 435/6
  See application file for complete search history.

(56) References Cited

U.S. PATENT DOCUMENTS

| | | | |
|---|---|---|---|
| 9,126,160 B2* | 9/2015 | Ness | B01F 3/0807 |
| 2005/0202489 A1 | 9/2005 | Cho et al. | |
| 2011/0086780 A1* | 4/2011 | Colston, Jr. | B01F 3/0807 |
| | | | 506/23 |
| 2012/0190032 A1* | 7/2012 | Ness | B01F 13/0062 |
| | | | 435/6.12 |
| 2013/0164789 A1* | 6/2013 | Schultz | B01F 3/0807 |
| | | | 435/91.2 |
| 2013/0344589 A1* | 12/2013 | Winkler | C12M 33/14 |
| | | | 435/309.1 |
| 2014/0193857 A1 | 7/2014 | Gray | |
| 2014/0272996 A1* | 9/2014 | Bemis | C12M 47/04 |
| | | | 435/6.12 |

FOREIGN PATENT DOCUMENTS

| WO | WO 2011/129697 A1 | 10/2011 |
|---|---|---|
| WO | WO 2012/142192 A2 | 10/2012 |
| WO | WO-2014089579 A1 | 6/2014 |

OTHER PUBLICATIONS

International search report and written opinion dated Apr. 21, 2014 for PCT/US2013/073957.

European search Report and Search Opinion dated Sep. 20, 2017 for European Patent Application No. EP13859774.5.

* cited by examiner

Fig. 4
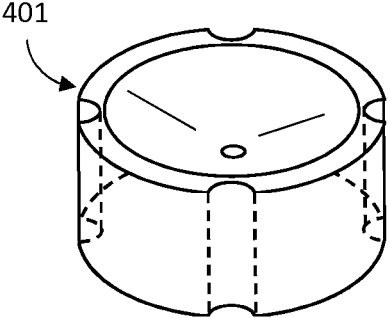 401
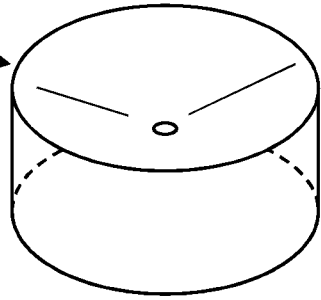 402
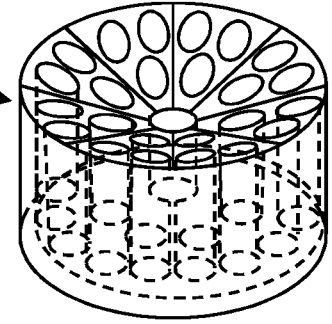 403
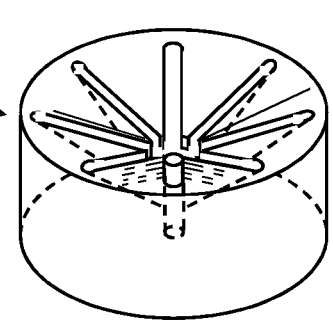 404

COMMON PORT EMULSION GENERATION SYSTEM

CROSS-REFERENCE TO RELATED APPLICATIONS

This application is a continuation-in-part of application Ser. No. 14/024,145, filed on Sep. 11, 2013, which claimed the benefit of U.S. Provisional Application No. 61/700,241, filed Sep. 12, 2012, and of U.S. Provisional Application No. 61/734,952, filed Dec. 7, 2012. The entire contents of each of these applications is incorporated herein by reference.

BACKGROUND OF THE INVENTION

1. Field of the Invention

The present invention relates generally to analytical tools and methods. More particularly, the present invention relates to apparatus, systems, and methods for forming emulsion droplets suitable for ude in ePCR and other analytical protocols.

Emulsions are used in a variety of biological laboratory applications. Chief among them is emulsion Polymerase Chain Reaction (ePCR), which has spurred the development of a number of commercial sample preparation platforms. There are two basic approaches to ePCR emulsion generation: agitate in a shaker or use a microfluidic system. Shaking reagents in a small disposable tube is inexpensive and precludes cross-contamination, but on the down side, the droplets generated are not uniform. Alternatively, microfluidic systems produce highly uniform droplets by passing fluids through microscopic, precision-manufactured pathways that are typically realized in planar layers of material. The major drawback of these systems is that are inherently expensive and do not scale well.

For these reasons, it would be desirable to provide alternative and improved methods, apparatus, and systems for performing ePCR in scalable and economically efficient platforms.

2. Description of the Background Art

US Patent Publication Nos. 2012/0190032 and 2011/0086780 describe systems for generation small droplet emulsions for performing ePCR and other procedures. See also U.S. Pat. No. 7,985,058 and WO 2012/142192.

SUMMARY OF THE INVENTION

The present invention embodies a technology that combines the benefits of both prior approaches and directly addresses the needs of ePCR sample preparation. The invention provides a precision microfluidic emulsion system that can be produced as an inexpensive disposable device. The preferred embodiment of the invention pairs precise but low-cost tubing and a simple injection-molded part to form a disposable device that is simple to use and produces highly uniform emulsions at a significantly lower cost per sample.

The present invention provides methods, articles, and systems for forming emulsion droplets from an aqueous phase and an organic phase. While the aqueous phase will typically comprise nucleic acids, such as double-stranded DNA, and the organic phase will comprise an oil which together form emulsion droplets that are suitable for performing ePCR, the present invention will be useful for forming emulsion droplets for any analytical or other purpose. The methods, articles, and systems of the present invention are particularly advantageous as they simplify the procedures used for forming ePCR emulsion droplets and allow for such emulsion droplets to be formed with relatively inexpensive equipment while producing droplets of highly uniform characteristics.

In a first aspect of the present invention, a method for forming emulsion droplets comprises introducing an aqueous phase and an organic phase into a reservoir. The reservoir may be an open reservoir free from internal barriers or partitions, allowing the aqueous phase and organic phase allowing the aqueous phase and organic phase to come into intimate contact and to eventually separate based on differences in their densities and other physical characteristics. Alternatively, the reservoir may have regions defined by internal barriers, partitions, or the like, which allow each phase to be inserted within the reservoir into the same and/or different regions created by the barriers or partitions. In all cases, the reservoir will include at least one common inlet port through which both phases can be introduced at a common region within the reservoir so that automated pipetting systems need only access a single location within the reservoir. Alternatively, in other embodiments, the two phases can be introduced into different regions within the reservoir but through the common inlet port, albeit with a possible loss of pipetting efficiency.

After the aqueous phase and the organic phase have been introduced into the reservoir, the phases will be caused to flow as separate streams from the reservoir. A variety of specific fluidic flow paths and components may be provided to effect such separation and flowing of the two phases. After the two streams flow from the reservoir, they are then combined to form the emulsion droplets which may be then be dispensed and collected, typically in a separate receptacle.

In ePCR and other DNA amplification methods, the organic phase will typically be introduced into the reservoir first followed by the aqueous phase. Flowing of the aqueous phase and the organic phase may be accomplished in a variety of ways. For example, the reservoir may be subjected to centrifuging in order to apply a force to the phases to cause them to flow through the fluidic pathways. Alternatively, the aqueous and organic phases may be caused to flow by applying a differential pressure across the reservoir. Typically, the differential pressure will be a positive pressure applied above the phases, e.g. through the common inlet port, within the reservoir. Alternatively or additionally, the differential pressure may be effected by applying a negative pressure at an outlet of the reservoir and the fluidic pathways.

Recombining the organic phase stream and the aqueous phase stream to form the emulsion droplets may also be effected in a variety of ways. Conveniently, the organic phase may be directed along an axial pathway which exits the reservoir. The aqueous phase which has separately exited the reservoir may then be directed along a lateral pathway that intersects with the axial pathway so that the phases combine to form the emulsion droplets in an efficient manner. In a specific embodiment described in detail below, the methods, the fluidic pathways are configured to achieve a coefficient of variation less than 50%, often less than 30%, and in many instances less than 10%, or better.

In a second aspect of the present invention, a method for forming emulsion droplets comprises introducing an aqueous phase and an organic phase into a single reservoir. By applying a force to the aqueous phase and the organic phase within the reservoir, a stream of the aqueous phase and a stream of the organic phase may be caused to flow from the reservoir. The separate aqueous phase stream and organic phase stream are then combined to form the emulsion droplets, and the emulsion droplets are dispensed into a receptacle which may be used for performing ePCR or other analyses on the emulsion droplets.

The aqueous phase and the organic phase are preferably introduced through a common inlet port on the reservoir, and the reservoir typically will have only a single common or other inlet port. The reservoir may be formed as part of a microwell plate having a plurality of individual reservoirs. Alternatively, the reservoir may be formed as a single, independent tubular or other member which consists of only a single reservoir. The methods are particularly useful for performing ePCR protocols, and the force may be applied by either centrifugation or applying a differential pressure as described above.

In specific embodiments, the organic phase is caused to flow along an axial pathway, and the aqueous phase is caused to flow along a lateral pathway, wherein the two pathways intersect to cause mixing to form the emulsion droplets. Typically, the emulsion droplets continue to flow along the axial pathway until they are dispensed into the receptacle. The droplets so formed may have a coefficient of variation less than 50%, usually less than 30%, often less than 10% or below.

After the emulsion droplets have been formed and collected in the receptacle, the droplets may be left in the receptacle and subjected to analysis. For example, the emulsion droplets may be thermocycled to perform ePCR or may be subjected to any other nucleic acid amplification procedure that can utilize such emulsions.

In a still further aspect of the present invention, an article for forming emulsion droplets comprises a body having an inlet port, an outlet and a reservoir configured to receive both an aqueous phase and an organic phase through the inlet port. A means for flowing an aqueous phase stream and a separate organic phase stream from the reservoir is provided, typically including a micro fluidic flow path within the body. Additionally, a means is further provided for combining the separated streams to form the emulsion droplets and dispensing them through the outlet. The means for flowing and the means for combining will typically comprise micro fluidic flow paths within the body, as described in more detail below.

In a specific embodiment, the means for separating the aqueous phase stream and the organic phase stream may comprise a hydrophobic barrier which allows the flow of the organic phase while redirecting the flow of the aqueous phase. In a specific example, the hydrophobic barrier comprises a conical element, optionally having vertical fins, which diverts the flow of droplets from the aqueous phase to a first fluidic pathway while allowing the flow of the organic phase to a second fluid pathway. Further fluidic pathways are provided in order to direct the organic phase along an axial pathway while introducing the aqueous phase into the flowing organic phase along a lateral pathway.

The articles may be formed individually in order to be removably replaced into a single receptacle. Alternatively, the articles may be formed as a group or plurality of articles in a configuration allowing their collective use, for example being formed in a micro well plate. In the latter case, the receptacle may be configured to mate with the micro well receptacle plate in order to receive and micro emulsion formed in each of the individual articles into individually isolated collection wells.

Systems according to the present invention may comprise any of the articles described above combined with a centrifuge configured to apply a centrifugal force to the article(s). The centrifuge will typically comprise a rotor configured to receive one or more receptacles and to apply a radial force along an axis of the receptacle when the rotor is spun.

In other embodiments, systems may comprise any of the articles described above in combination with a differential pressure generator which may be connected to the inlet port and or outlet port of the reservoir in order to apply a differential pressure to cause flow of the organic phase and the aqueous phase through the fluidic pathways of the articles.

BRIEF DESCRIPTION OF THE DRAWINGS

FIG. 4 is an isometric view of various embodiments of the semi-permeable, conical barrier that separates and directs each fluid to a separate fluidic pathway, in accordance with the present invention.

DETAILED DESCRIPTION OF THE INVENTION

Figure 1:
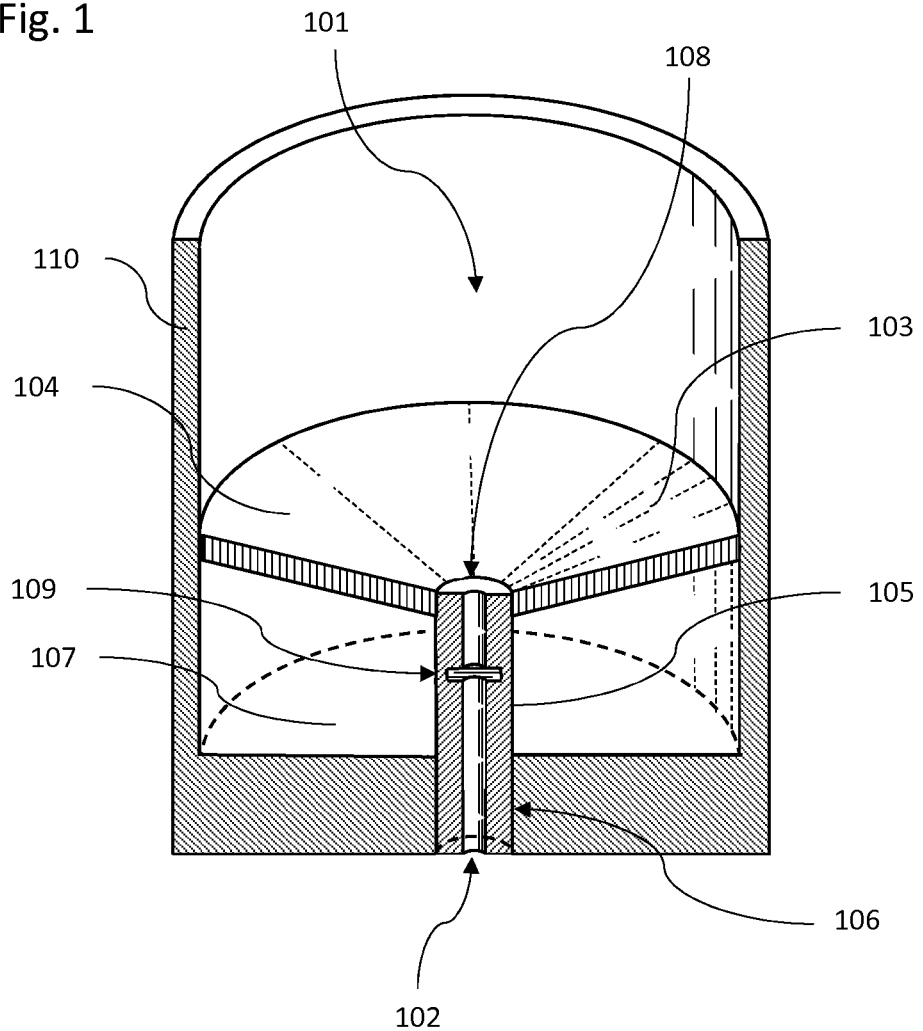
FIG. 1 is an isometric, cross-sectional view of an exemplary embodiment of a single-reservoir droplet generation system, in accordance with the present invention.

The present invention comprises a system, apparatus, and methods for generating emulsions for droplet-based assays. The advantages of the present invention over existing methods for generating emulsions include the ability to generate highly uniform emulsions at lower costs and with a lower propensity for errors. Various embodiments of the present invention are designed to be disposable units that fit within the existing footprint of high-throughput systems, such as microcentrifuge tubes and multiwell plates. The present invention offers a means of combining an organic phase and an aqueous phase through a single common inlet, directing each phase to a separate fluidic pathway, recombining the two phases to form emulsion droplets, and exiting the emulsion through an outlet to a receptacle that can be removed, allowing the emulsion to be further processed.

In ePCR and other DNA amplification methods, the organic phase will typically be introduced into the reservoir first followed by the aqueous phase. Flowing of the aqueous phase and the organic phase may be accomplished in a variety of ways. For example, the reservoir may be subjected to centrifuging in order to apply a force to the phases to cause them to flow through the fluidic pathways. Alternatively, the aqueous and organic phases may be caused to flow by applying a differential pressure across the reservoir. Typically, the differential pressure will be a positive pressure applied above the phases, e.g. through the common inlet port, within the reservoir. Alternatively or additionally, the differential pressure may be effected by applying a negative pressure at an outlet of the reservoir and the fluidic pathways.

Recombining the organic phase stream and the aqueous phase stream to form the emulsion droplets may also be effected in a variety of ways. Conveniently, the organic phase may be directed along an axial pathway which exits the reservoir. The aqueous phase which has separately exited the reservoir may then be directed along a lateral pathway that intersects with the axial pathway so that the phases combine to form the emulsion droplets in an efficient manner. The emulsion droplets are dispensed into a receptacle which may be used for performing ePCR or other analyses on the emulsion droplets. In a specific embodiment described in detail below, the methods, the fluidic pathways are configured to achieve a coefficient of variation less than 50%, often less than 30%, and in many instances less than 10%, or better.

The requirement to fill only one reservoir radically simplifies the protocols required to generate an emulsion via the present invention as compared to other existing methods. Rather than filling multiple reservoirs with various phases, the article disclosed here requires only a simple ordering of two phases, organic and then aqueous, with lower volumes required of each. The aqueous phase will typically comprise nucleic acids, such as double-stranded DNA, the organic phase will comprise an oil.

In its preferred embodiments, the article described in the present disclosure, whether incorporated into single test tubes, multiwell plates, or proprietary cartridges, can be injection-molded as part of a single unit. This results in significantly reduced manufacturing costs, thereby enabling a disposable device.

I. Definitions

Inlet: An opening in the device, such as the open top of a container, that accepts reagents.

Reservoir: A bulk fluid retention area; the internal space of a container.

Semi-permeable barrier: A structure that directs uses their innate physiochemical properties to separate fluid one and fluid two into distinct fluidic pathways.

Slotted tube: A tubular structure or pipe with an outer diameter of not more than 1 mm and an inner diameter of not more than 1 micrometer that is pierced by a lateral hole. The lateral hole runs perpendicular to the tube central axis and is dimensioned such that it fully bisects the inner diameter but not the outer diameter of the tube; the lateral hole is flanked on two sides by material that provides structural support to keep the tube segments from separating.

Lateral hole: A window shaped through-hole in a Slotted tube.

Pierced tube upper: The portion of a Slotted tube that is upstream of the Lateral hole.

Pierced tube lower: The portion of the Slotted tube that is downstream of the Lateral hole.

Tube fixture point: The point at which the outer diameter of the tube is physically attached to the device substrate.

Outlet: An opening in the device where fluids emerge, for example, as an emulsion of a first fluid and a second fluid.

Centrifuge tube: A tube designed for use with fluids in a centrifuge. As an example, microcentrifuge tubes are typically disposable, polymeric, capped tubes with an internal volume of 2 milliliters that are shaped to fit into standard centrifuge rotors.

Multiwell plate: A device comprised of a multitude of individual chambers that is broadly conforming to the specification ANSI/SLAS 2-2004 (formerly recognized as ANSI/SBS 2-2004). Interchangeable with microplate and microwell plate.

Cartridge: A polymeric device containing at least one complement of all of the elements comprising single-reservoir emulsion generation system or more slotted tubes.

II. System Architecture

The present invention defines an article composed of 1) a single reservoir (also the inlet) to contain two fluids, an aqueous phase and an organic phase, 2) a semi-permeable barrier that enables two fluidic pathways from the single reservoir, 3) a slotted tube that recombines the two phases to create an emulsion, and 4) an outlet to a separate, removable receptacle. The article as described in this disclosure may be contained within a number of different devices, including an insert to a standard test tube, a multiwell plate, or a proprietary cartridge. This disclosure discusses the various aspects and embodiments of the article and its preferred embodiments.

To generate an emulsion suitable for performing ePCR or other assays typically requires the combination of two fluids, one aqueous and the other organic. Existing systems generally have separate reservoirs for each fluid and microfluidic pathways that cause the two fluids to combine at some further point in the system. The present invention utilizes a single reservoir 110 with a single inlet 101 and a single outlet 102, as illustrated in FIG. 1. The organic phase is first added through inlet 101 to fill reservoir 110, then the aqueous phase is added through inlet.

A semi-permeable barrier 103 comprises the lower portion of the reservoir. Its upper surface allows the organic fluid to pass through it, while retaining the aqueous fluid at its upper conical surface 104. A slotted tube 105 is attached to the tube base 106 at the bottom 107 of the reservoir and extends upward from the outlet to the upper surface of the barrier. The inner diameter 108 of the tube is open to the upper surface of the barrier while the slot 109 is positioned such that it is only accessible to the fluid below the barrier. The end of the tube forms the outlet of the article.

Figure 2:
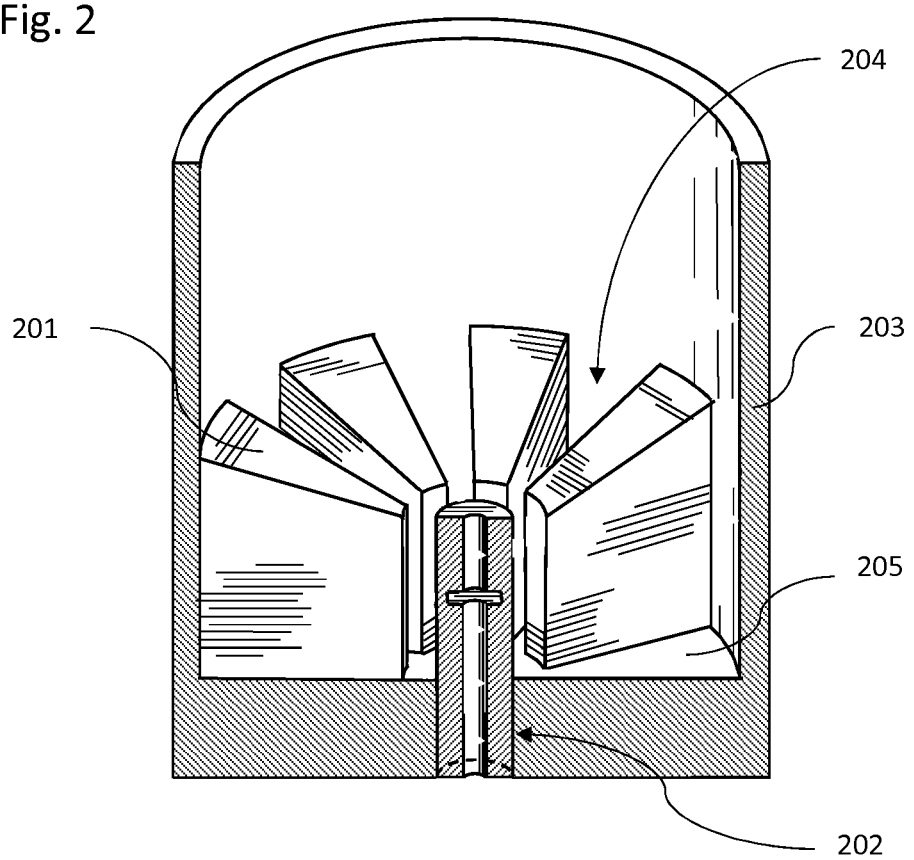
FIG. 2 is an isometric, cross-sectional view of another embodiment of a single-reservoir droplet generation system, in accordance with the present invention.

FIG. 2 illustrates a preferred embodiment of the invention where the semi-permeable barrier 201 and slotted tube mount 202 are integral to the reservoir 203. Advantageously, this design can be realized in a single piece using standard thermoplastic injection molding processes. The features comprising this architecture may be fully drafted, with the funnel features, reservoir structure, and tube mounting being formed from a single mold without side action. Even more advantageously, this architecture may also be produced as a collection of systems (e.g., as a multiwell plate) using a standard single-shot injection molding process.

In this preferred embodiment, an array of narrow channels 204 extend upward (in the Z axis) from the lower surface of the reservoir 205 as a closely packed collection of columnar features that together comprise a funnel-shaped upper surface.

Figure 3:
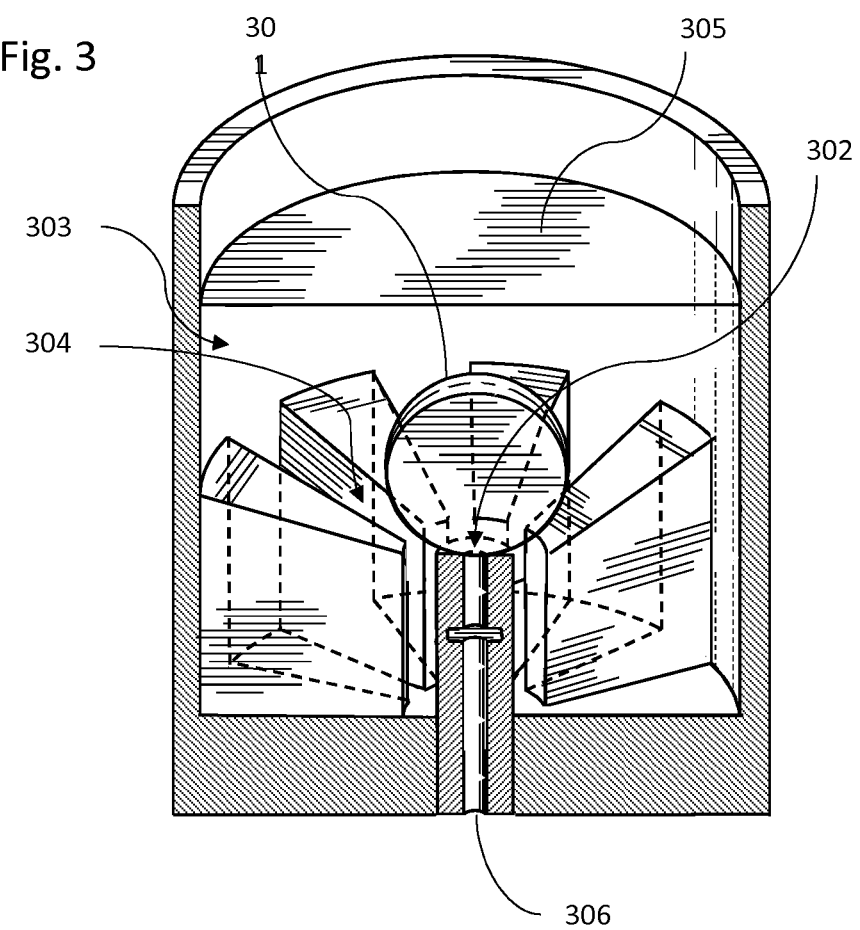
FIG. 3 is a view of FIG. 2 further showing two fluids in a single reservoir.

FIG. 3 illustrates the separation function provided by the semi-permeable barrier. The relative positions of the two fluids in the device are depicted. The spherical partition 301 rests at the center of the semi-permeable barrier 302 and the organic phase 303 occupies all internal spaces of the reservoir and including the internal spaces defined by the barrier, including radial channels 304 and up to the upper fluid surface 305.

Despite the two phases comingling in a single reservoir, aqueous partitions are retained above the surface of the barrier by a combination of forces. First, gravity acts to draw the heavier aqueous fluid downward toward the barrier surface. Second, the physiochemical properties of the organic fluid in combination with the aqueous phase ensures that the aqueous reagent forms spherically shaped partitions due to surface tension where it is in contact with the organic phase. Moreover, those partitions resist breakup; larger sized partitions represent the lower energy state, and thus aqueous partitions will not tend to dissociate during operation of the device. Third, the narrow channels radiating from the center of the funnel-shaped barrier are too narrow to allow aqueous partitions to enter.

FIG. 3 illustrates how the limited width of the channels, the hydrophobic nature of the organics, and the unique geometries of the barrier ensure that each partition comprising the aqueous phase experiences the semi-permeable barrier as a contiguous, sloped surface to assure that each phase follows a separate fluidic pathway; aqueous partitions 301 displace organic fluid as they ultimately come to rest at the top of the slotted tube 302. In this way, each fluid has access to a unique fluid pathway as they flow toward the outlet 306.

Figure 5:
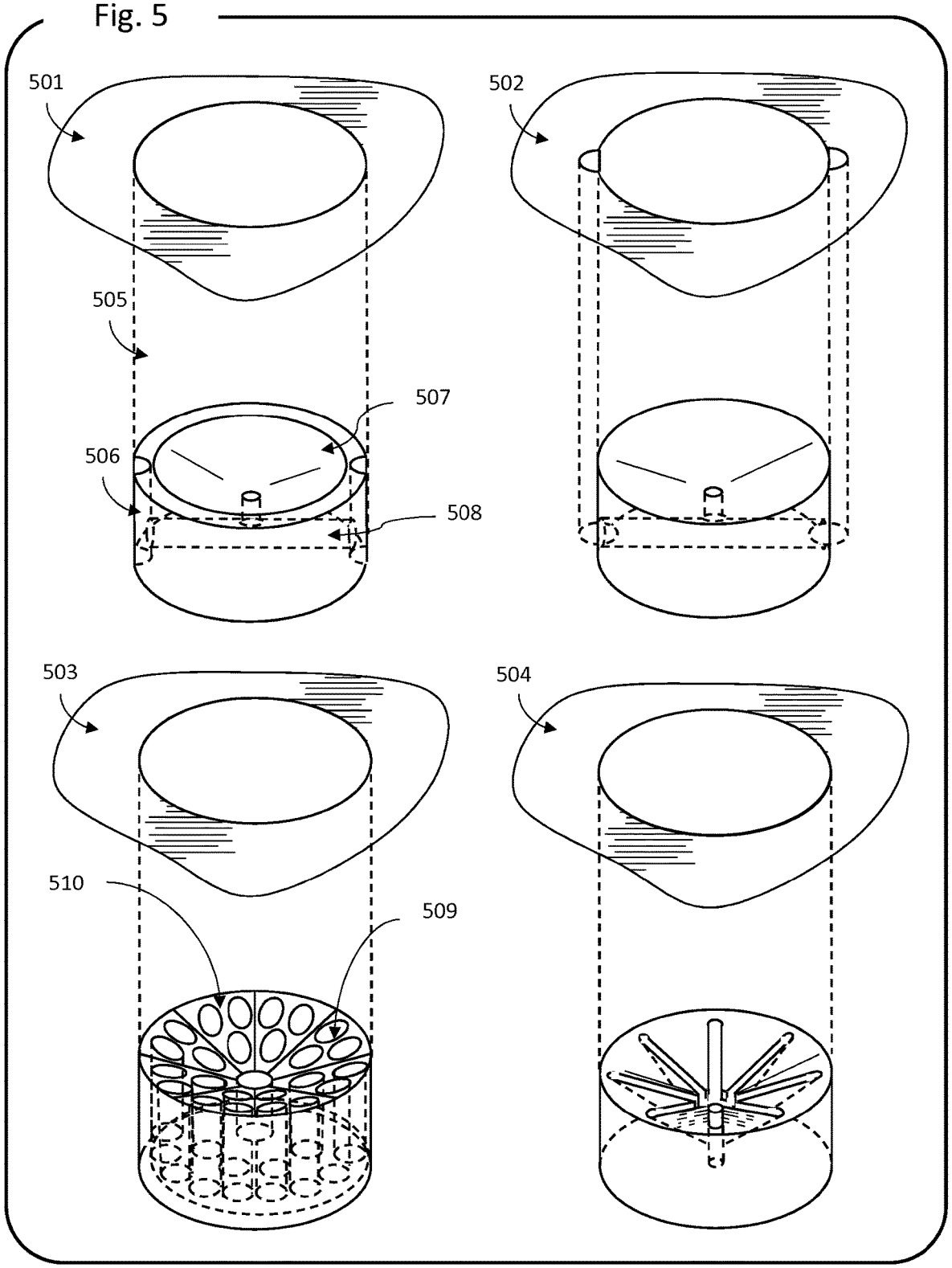
FIG. 5 is an isometric illustration of various embodiments of the semi-permeable, conical barrier, as in FIG. 4, united with various exemplary embodiments of the reservoir, in accordance with the present invention.

FIG. 4 illustrates an exemplary collection of selective barrier designs in accordance with the invention and FIG. 5 shows them in situ paired with a complementary reservoir. Each of the examples provided offers a means for selectively separating the organic and aqueous reagents into two distinct flow paths. In general, organic fluid above the aqueous partition in the reservoir must pass down and around the aqueous partition. For simplicity of illustrating the point, consider that in every case there is a vertical and horizontal component to the flow, and each of the designs provided has a radial and uniform pattern with aqueous fluid directed toward an axial pathway at its center. This collection of barrier designs is not exhaustive and a multitude of useful variations in the themes outlined here are possible and are all aspects of the present invention.

Given that the aqueous component is retained at the center of the semi-permeable surface, variation in the design is primarily about the flow paths of the organic fluid. In examples 401 and 402, and their corresponding reservoirs 501 and 502, organic fluid flows down from the reservoir 505 along vertical channels 506 positioned at the edge of the reservoir adjacent a surface 507, and then horizontally under the barrier in a lateral pathway 508 to access the slot. In a preferred embodiment of the invention, example 403 and corresponding reservoir 503 illustrate a pattern of vertical shafts each having a through-hole 509 that provide for fluid communication between the top surface 510 of the barrier down through the structure of the barrier to a volume that is open to the slot. In a more preferred embodiment of the invention, 404 and 504, channels in the upper fluidic path allow for both the vertical and horizontal components of the flow to occur below the aqueous partition(s) without penetrating the selective barrier.

Fluids within the device are moved by pressure differentials. Motive forces can be generated by a differential gas pressure, direct force, or centrifugation. Such forces can be achieved by employing compressed gases or a vacuum pump, a piston, or a centrifuge. Some embodiments of the invention are more disposed to a particular device format. For example, in some instances it may be practical or convenient to incorporate the system into a cartridge. In other cases, it may be more advantageous to deploy the disclosed invention as a multiwell plate or centrifuge tube insert, discussed further below.

Figure 6:
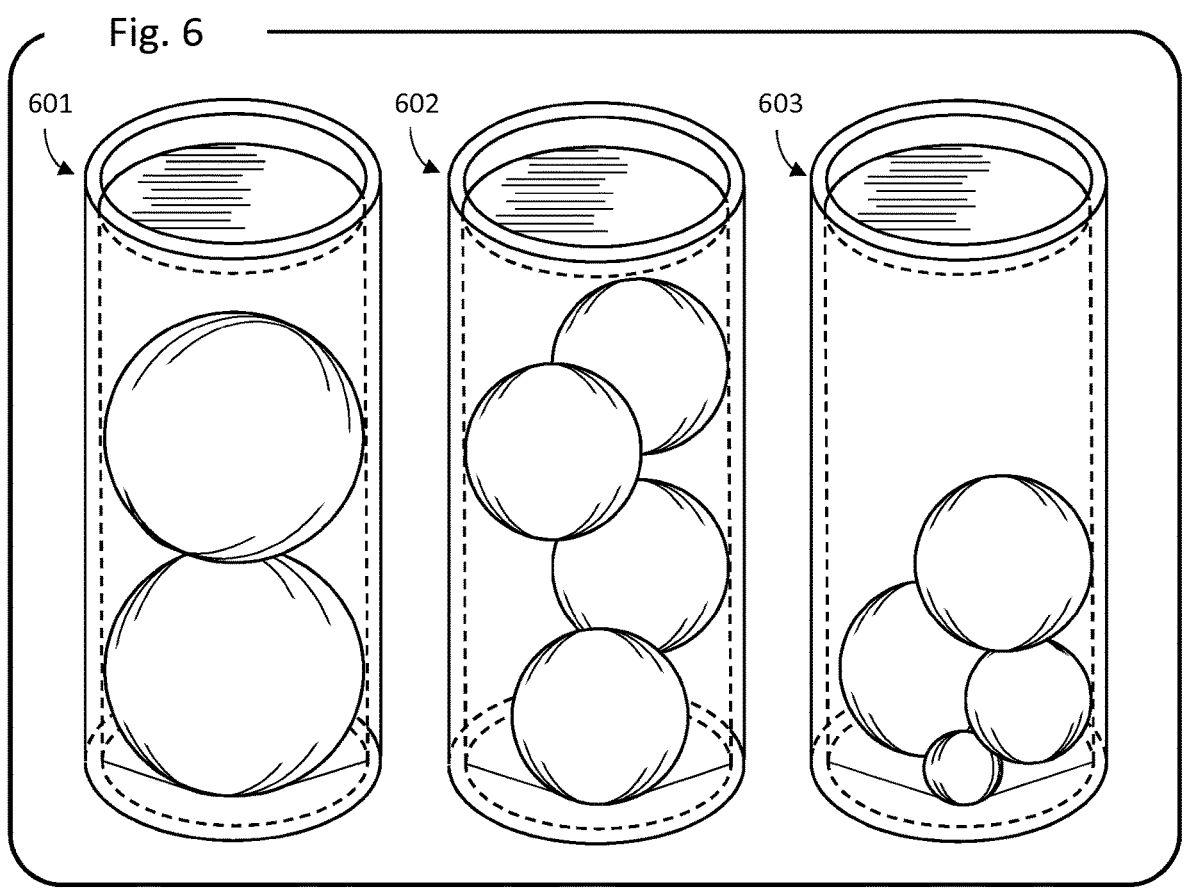
FIG. 6 is an isometric illustration of various examples of how fluids one and two remain separate yet in intimate contact within a given reservoir, yet separated, in accordance with the present invention.

FIG. 6 illustrates the behavior of multiple aqueous partitions within the reservoir in different possible scenarios 601, 602, and 603. In each case, the physiochemical properties of the two fluid phases as well as the design characteristics of the reservoir and the semi-permeable barrier ensure that the aqueous partitions maintain their integrity and flow through the desired fluidic pathway, regardless of the number or shape of the aqueous partitions.

Figure 7:
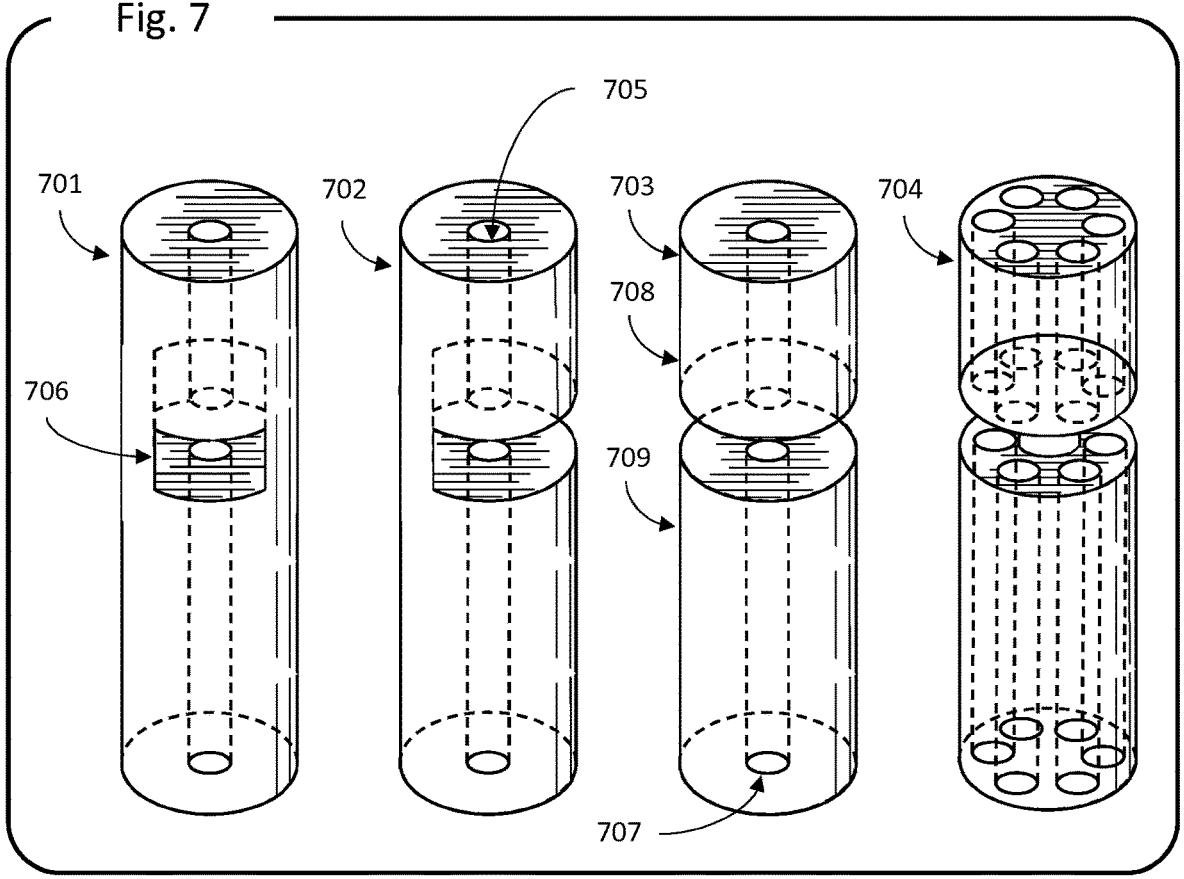
FIG. 7 is an isometric view of various embodiments of the segmented tube, in accordance with the present invention.
Figure 8:
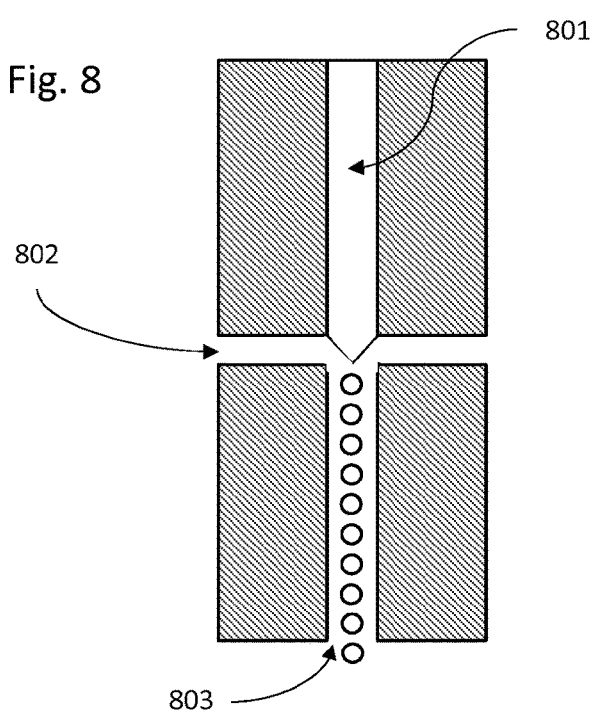
FIG. 8 is a cross-sectional illustration of the intersecting fluidic pathways that is the exemplary means of droplet generation for each embodiment represented in FIG. 7.

FIG. 7 illustrates various embodiments of the slotted tube 701-704, each of which is characterized by a complete bisection of the inner diameter 705, 801 of the tube and wide access for the fluidic path from the bottom of the reservoir, through the slot or cut 706, 802, and into the flow through the inner diameter of the tube to exit through the outlet 707, 803, as shown in FIG. 8.

Figure 9:
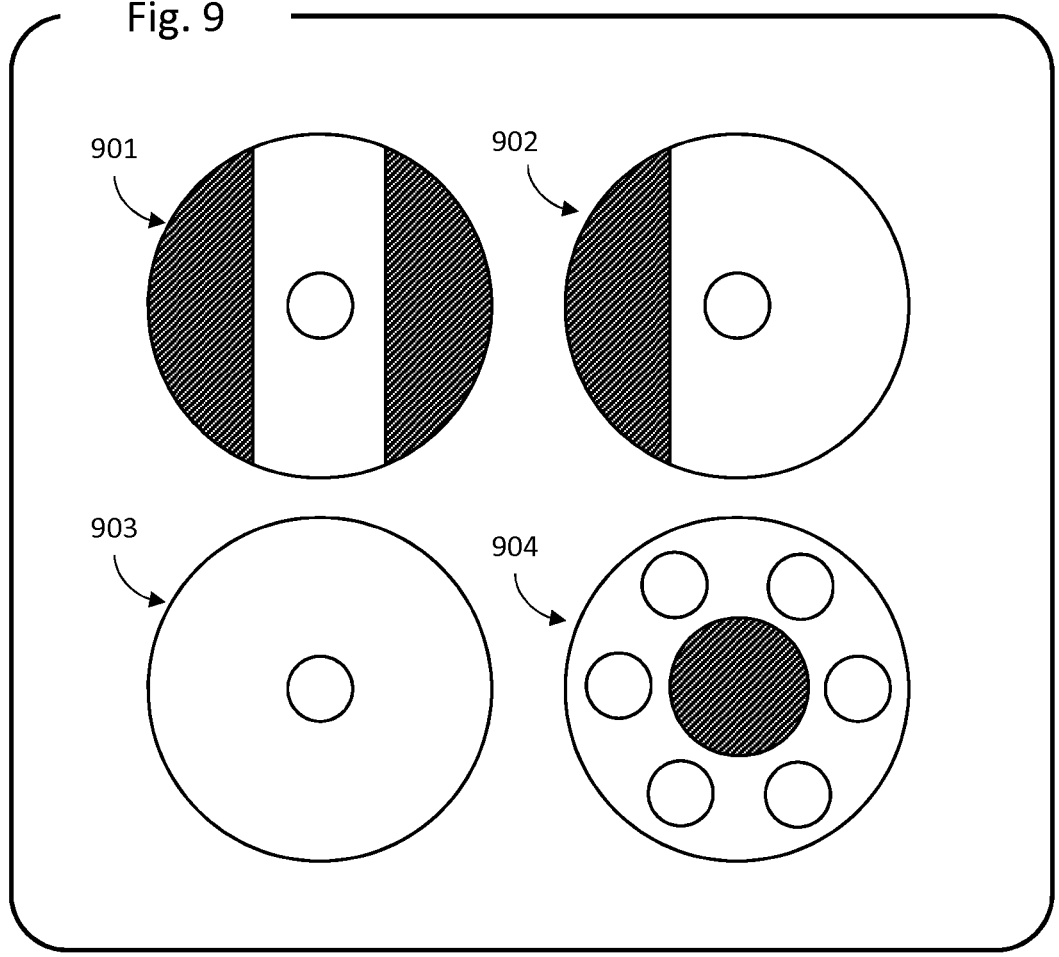
FIG. 9 is a cross-sectional view of each of the various correspondingly numbered embodiments of the segmented tube represented in FIG. 7.

Embodiment 901 in FIG. 9 shows a window through-cut, a preferred embodiment of this aspect of the present invention. Embodiment 902 shows a partial through-cut. Embodiment 903 shows a complete bisection, the least preferred embodiment as it requires both sections of the slotted tube to be anchored separately. Embodiment 904, another preferred embodiment, illustrates a multi-channel tube capable of generating multiple droplets in parallel connected by a central shaft. FIG. 9 is a cross-section view of the embodiments presented in FIG. 7, illustrating the retained material that anchors (or not) the upper 708 and lower 709 sections of the slotted tube.

Figure 10:
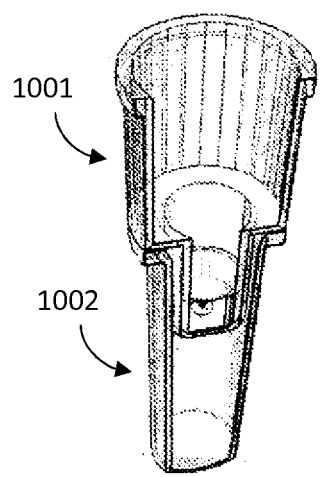
FIG. 10 is an isometric, cross-sectional view of an exemplary embodiment of the article configured for centrifugation, illustrating a reservoir seated within a standard microcentrifuge tube, in accordance with the present invention.
Figure 11:
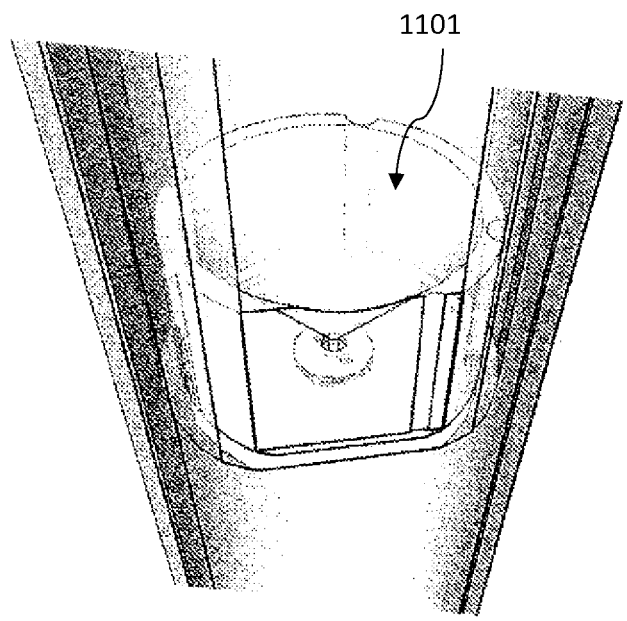
FIG. 11 is an enlarged, isometric, cross-sectional view of the semi-permeable, conical barrier illustrated in FIG. 10.
Figure 12:
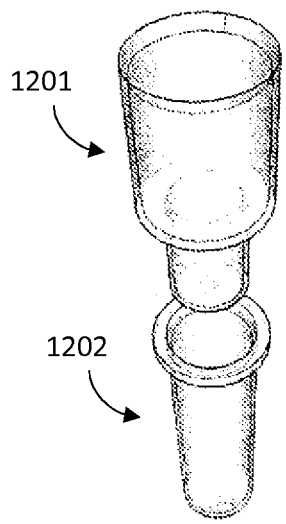
FIG. 12 is an isometric view illustrating the insert and the removable, receptacle microcentrifuge tube comprising the assembly as in FIG. 10.
Figure 13:
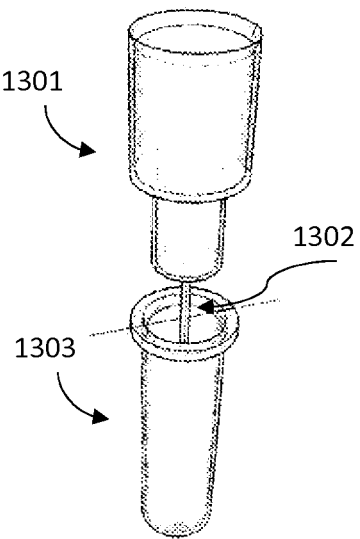
FIG. 13 is an exploded view of an exemplary embodiment of the article configured for centrifugation illustrating the relative positions of the inert, slotted tube, and receptacle, in accordance with the present invention.

In accordance with the invention, FIGS. 10 through 13 illustrate a centrifugally operated device. FIG. 10 depicts the device as an insert 1001 seated in a receptacle tube 1002. FIG. 11 is a more detailed view of the semi-permeable barrier 1101 with a flow pattern as described in the first example in FIG. 4. To use the device, organic fluid is added first, followed by aqueous fluid, prior to rotation in a swinging arm or a 45-degree fixed rotor centrifuge. After centrifugation, the insert 1201 can be removed from the receptacle tube 1202, as in FIG. 12, so that the resultant sample can be further processed, e.g. amplified using thermocycling or another process. An exploded view comprising the reservoir 1301 and integral semi-permeable barrier structure (not shown); tube 1302 and receptacle 1303 comprising this exemplary embodiment of the invention are illustrated in FIG. 13.

Figure 14:
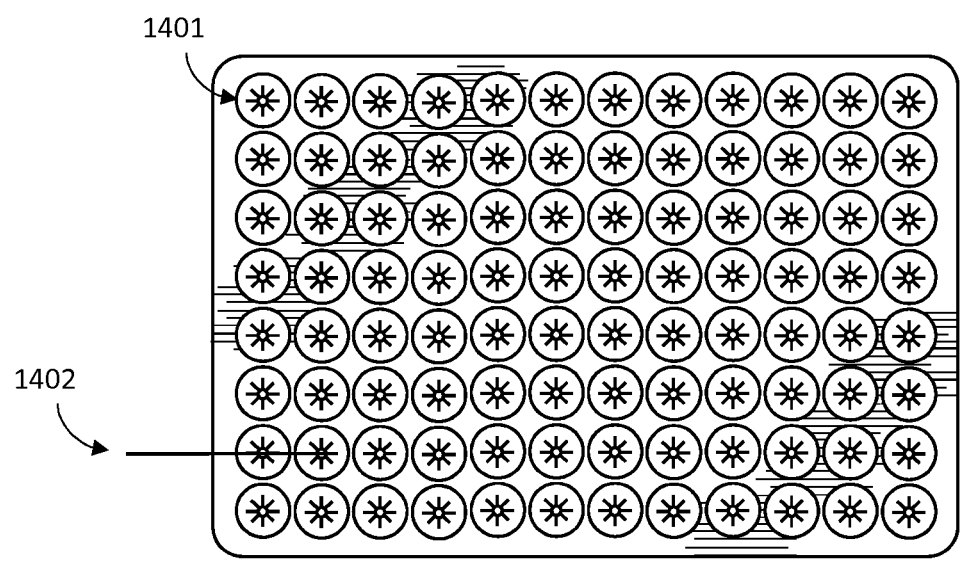
FIG. 14 is a top view of an exemplary embodiment of the article as a multiwell plate, in accordance with the present invention.
Figure 15:
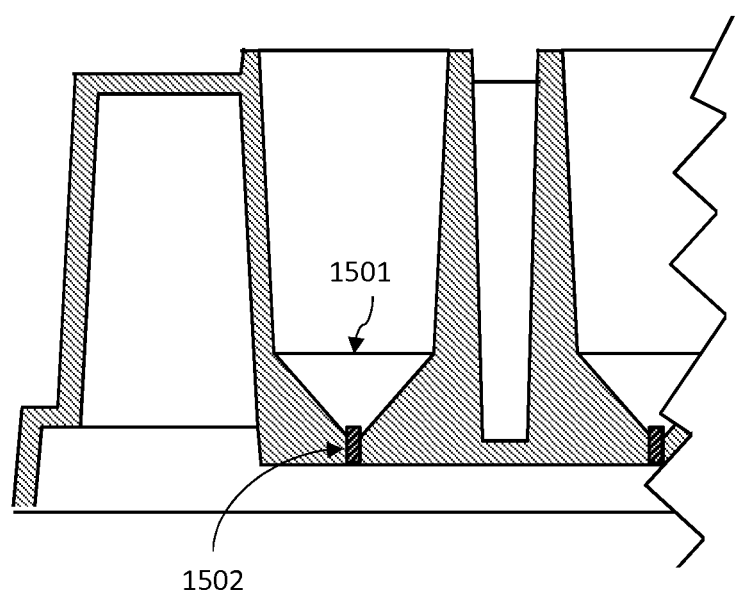
FIG. 15 is a cross-sectional, partial view of the embodiment of the article illustrated in FIG. 14.

In a further embodiment, the invention can be incorporated within a multiwell plate, as shown in FIG. 14. In this embodiment, each well 1401 on the plate is a separate instance of the invention. FIG. 15 provides a partial view in cross-section of a well with the semi-permeable barrier 1501 and slotted tube 1502 in situ along line 1402.

Figure 16:
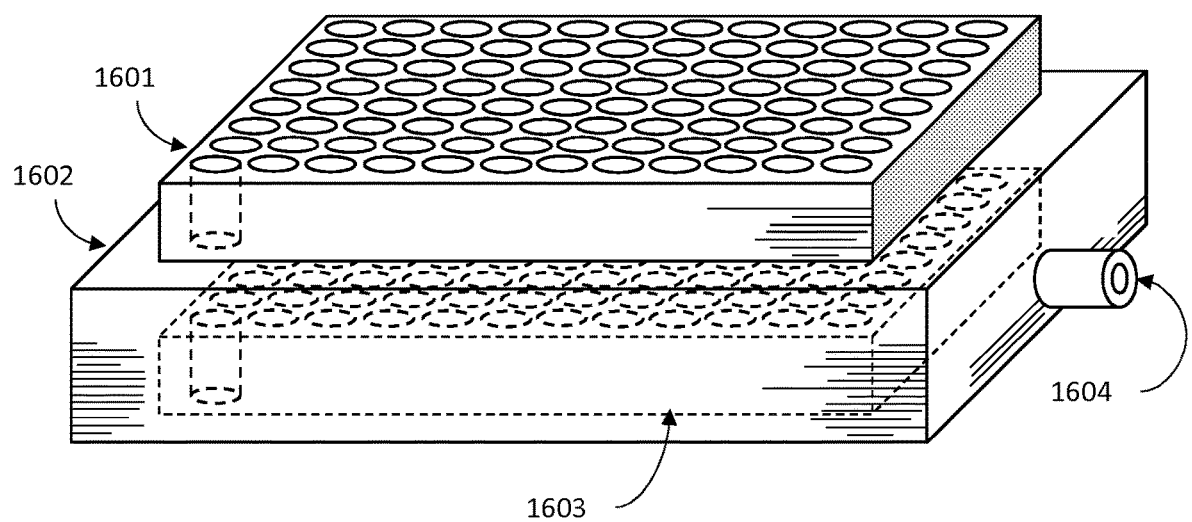
FIG. 16 is an isometric illustration of an exemplary embodiment of the article as in FIG. 14 seated on a typical laboratory vacuum manifold and positioned above a corresponding, receptacle multiwell plate.

FIG. 16 further elaborates on the embodiment of the invention as in FIG. 14, illustrating the embodiment of the invention in multiwell plate format 1601 with a vacuum manifold 1602 and standard multiwell plate receptacle 1603. Application of differential pressure via the vacuum manifold via connector 1604 provides the motive force to generate the emulsion. Once the emulsion has been generated, the multiwell plate receptacle can be removed from the article described so that the resultant sample can be further processed, e.g. amplified using thermocycling or another process.

Figure 17:
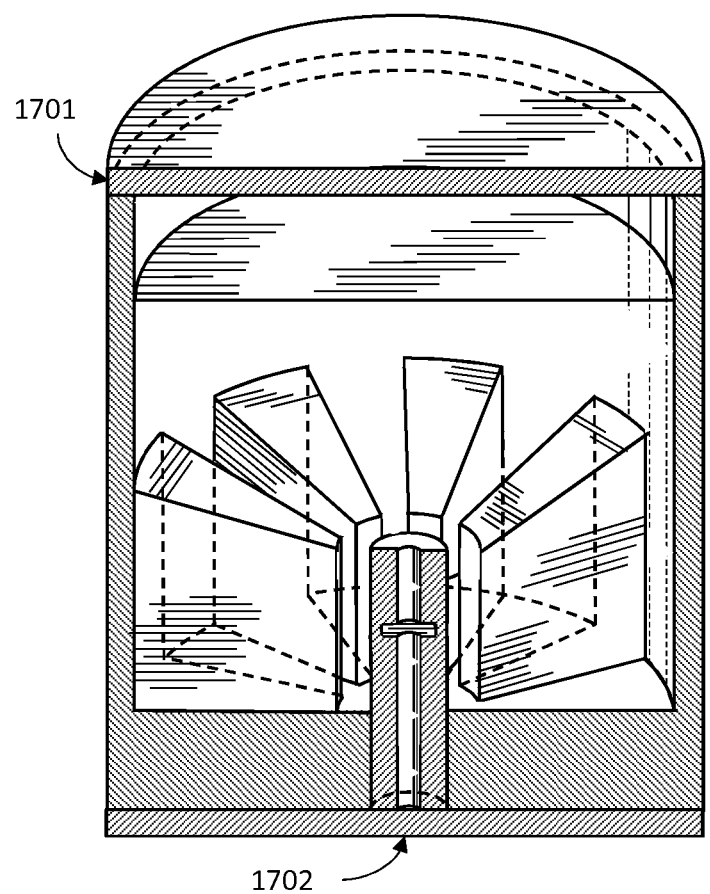
FIG. 17 is an isometric, cross-sectional view of an embodiment of the present invention as in FIG. 2 illustrating protective films sealing the top of the inlet and the outlet, in accordance with the present invention.

An important element of producing uniform emulsions from small fluid volumes for the purposes of ePCR or other assays is ensuring the apparatus or device used to generate the emulsion remains free from particulates or other contaminates. The present invention foresees the ability, in any embodiment, to apply a pierced or removable film over the inlet 1701, outlet 1702, or both, as shown in FIG. 17. The advantages of film applied in either or both locations are that contaminants cannot be introduced accidentally and that embodiments of the invention can be pre-loaded with a first fluid prior to use.

With reference to FIG. 13, in a capillary tube version, a capillary tube is positioned such that a first fluid flows under centrifugal force through the capillary and into a second fluid. The capillary will bend under centrifugation, which will have the effect of aligning the distal end of the capillary with the flow of the first fluid emerging from it. A notch in the tube (not shown) would promote droplet generation by allowing the second fluid to interrupt, periodically, the flow of the first.

Embodiments of the present invention provide a method and apparatus for the controlled production of small droplets having a narrow size distribution. Embodiments of the present disclosure also provide a method of manufacturing an improved apparatus cost-effectively using readily available and inexpensive materials.

According to embodiments of the present invention, an emulsion is formed using the presently disclosed apparatus by mixing two fluids in a microfluidic junction embedded between two fluid chambers. A first fluid chamber is in fluid connection with one distal end of a microfluidic channel; a second fluid chamber is in fluid connection with an open gap in the microfluidic channel; a second distal end of the microfluidic channel is in fluid connection with the exterior of the device.

The two fluid chambers and associated microfluidic channel are colocated with, and together comprise, a housing body. The first chamber is in fluid communication with a fluid inlet port that forms an opening on the housing body; the second fluid chamber is in fluid connection with the first fluid chamber. The two chambers are in fluid communication with each other.

The fluid chambers are positioned and shaped such that when a first fluid is introduced to the inlet port, it enters the first chamber, and when a second fluid is introduced to the inlet port, it overflows or otherwise fills both fluid chambers. In this way (using the example of an emulsion PCR sample prep), aqueous reagents will settle into the first chamber and stay settled there even as oil is introduced to the inlet port to overlay the water in the first chamber and overflow into the second chamber. The two fluids stay in place largely because of surface characteristics, small geometrical features, differences in density, and immiscibility. The two chambers comprising the bulk of the housing body are interconnected so that when a pressure is applied to the inlet port of the first, fluid chamber, the second fluid chamber experiences a nearly equal, similar, or related internal pressure.

If the housing is placed on a syringe tip providing gas or fluid pressure, the two fluids experience very nearly equal pressures.

If the housing is placed in a centrifuge to provide centrifugal force, the two chambers may be connected by a head space or be in fluid communication with each other. If only the head space is shared, then their pressures are related by virtue of spinning at a shared speed; if in fluid communication then their pressures will be nearly equal with the difference being a function of their differing densities.

If the housing is placed in a base station providing gas or fluid pressure to the fluid inlet port, then the pressures of the two fluids are nearly equal.

The first fluid flows from the first fluid chamber into one end of a microfluidic channel and across a gap that is open to a second fluid chamber. The first fluid exits the microfluidic channel at the gap and as it traverses the gap to enter the second segment of the microfluidic channel it is immediately reformed into a cone as the second fluid that fills the gap is introduced from the space surrounding the tubes and flows into the lower capillary. The two fluids squeeze together to form a coaxial flow at the open end of the second capillary. The gap functions as a fluid junction. The coaxial flow can either break into droplets at the junction or continue as a coaxial stream that breaks into droplets later. The inner flow is comprised of the fluid exiting the first microfluidic channel and the second fluid being introduced from the gap between the microfluidic channels to form the outer sheath of the coaxial flow. For emulsion PCR, the inner flow (first fluid) contains the aqueous PCR reagents, and the outer flow (second fluid) is comprised of oil.

The method of the invention comprises (a) forming droplets of a first, liquid in a coaxial laminar flow of a second liquid, each droplet having a volume of between 1 fL and 1 nL, and wherein the first and second liquids are, at most, sparingly soluble (more preferably, substantially immiscible) in one another. Laminar flow is defined as a non-turbulent fluid flow.

The method and apparatus are particularly well-suited for making a substantially monodisperse collection of droplets having a mean volume of from 1 fL to 1 pL; for example, a monodisperse collection of droplets has a normal distribution of droplet diameters, with a mean diameter D of from 1 micrometer to 100 micrometers, and a coefficient of variation of 3%.

In one embodiment of the invention, substantially uniformly sized droplets are generated using capillary microfluidic pathways, gap junctions, piezo actuators, software, and electronics. By controlling the electric impulses to the actuator(s) via a computer control system, very precisely sized droplets can be produced in a laminar flow of a substantially immiscible, or at least no more than sparingly soluble, liquid. For example, droplets for PCR are formed by coextruding two fluids coaxially in a microfluidic pathway with the inner fluid containing an aqueous solvent containing PCR reagents dissolved, dispersed or suspended therein through the fluid gap junctions of the apparatus into a laminar flow of water or other non-aqueous medium in the transverse liquid channels, and collecting the resulting droplets for further processing. Advantageously, the droplets' narrow size distribution makes each droplet functionally interchangeable, and the number or concentration of reagents within the droplets can be described by a Poisson distribution.

In another embodiment of the invention, the emulsion production system is a stand-alone bench top unit. The benchtop unit consists of a means to supply one or all of the following: a pressure source, pressure control, a fluid source, fluid flow control, a fluid filtration capability, a mating fixture for the inlet port, a mating fixture for the outlet port, physical support for the disposable component, a lathing mechanism to retain the disposable component, a computer based user interface, a touch screen, a computer based device control system, an ultrasonic pulse generator, and a waste container.

By oscillating the pressure of the oil in the area of the gap, higher pressures are experiences in the junction periodically. These higher pressures force the flow of water in the center of the tube to reduce in diameter, pinching the flow of water. Those narrowed areas ultimately become neck that divide the flow of water into droplets. Synching the waves to a piezo element allows the user to time the droplets and to visualize their formation.

Cross section view of the space between the two capillary tubes shows that there is a flow path that is similar to a T-junction. The first fluid is introduced from the top tube, and flows through the gap, where a second fluid is allowed to enter the lower capillary tube. The two fluids flow into the lower capillary tube coaxially. Droplets are formed at a point after or in the junction area.

As the device fills it becomes pressurized. By virtue of the shared pressure source of the tip, the fluids are very nearly equally pressurized when they reach the droplet forming capillary junction.

The distance that separates the two capillary segment ends is approximately equal to the diameter of the internal diameter.

Existing devices may include similar geometries of the flow junction, but flow junctions themselves are not new. Other disclosures do not, teach the manufacturing method. Instead, those other devices and methods teach the use of a capillary as simply a means for moving fluids to different locations such as temperature control devices and the like, but they never actually suggest using a capillary tube to create the junction.

FIG. 8 shows two capillary tubes separated by a small gap, but with two fluids flowing, the first flowing in from the top capillary tube and the second laterally at the gap, and forming droplets in accordance with the invention, according to embodiments of the present invention.

EXAMPLE 1

One embodiment of the invention is an emulsifier unit. The device is used to combine two or more fluids into an emulsion. The disposable element of the device is comprised of a first fluid inlet port in fluid communication with a pressure chamber in fluid communication with the inlet side of one or more fluid gap junctions, a second fluid inlet port in fluid communication with the open area between the microfluidic channels. The non-disposable elements of the device comprise one or more temperature zones in order to maintain uniform viscosity and fluid flow. A product outlet port allows an emulsion stream to exit the unit.

EXAMPLE 2

A device as in Example 1 wherein the fluid gap junction or multitude of fluid gap junctions is capable of producing an emulsion wherein the droplets have a coefficient of variation of less than 10%.

EXAMPLE 3

A device as in Example 1 wherein the fluid gap, unction or multitude of fluid gap junctions is capable of producing an emulsion wherein the droplets have a coefficient of variation of less than 7%.

EXAMPLE 4

A device as in Example 1 wherein the fluid gap junction or multitude of fluid gap junctions is capable of producing an emulsion wherein the droplets have a coefficient of variation of less than 5%.

EXAMPLE 5

A device as in Example 1 wherein the product outlet port is in fluid communication with the next step in the workflow process, such as in a continuous flow emulsion PCR system. In one embodiment, of such a system, droplets flow directly from the emulsion generating unit into a thermocycling platform. In another embodiment the emulsifier unit is a modular component of a sequencing platform. In a continuous flow system the microfluidic elements of a complex device may be in close physical proximity to one another and may even occupy the same microfluidic chip.

EXAMPLE 6

A device as in Example 1 wherein the outlet port is directed into one or more capture containers or wells on a multi-well plate. In one embodiment of the invention, droplets emerging from the product exit port may be directed dropwise into one or more liquid containers, such as a microtube. In another embodiment of the invention the emulsifier unit is integrated with a fluid handling station such that liquid emerging from the product exit port is distributed among one or more liquid containers, such as multi-well plates.

EXAMPLE 7

A method for sample preparation for emulsion PCR wherein the sample format is an oil-in-water emulsion with uniform droplet diameters.

EXAMPLE 8

A method as in Example 7 wherein the droplet or multitude of droplets comprising an emulsion contains at least one solid bead. In one embodiment, the bead may be of any type as designated by an emulsion PCR reagent kit. In another embodiment, the droplet or multitude of droplets does not contain a solid bead.

EXAMPLE 9

A method as in Example 7 wherein the droplet car multitude of droplets comprising an emulsion contains at least one of the reagents necessary to perform a PCR reaction. Such PCR reagents may include nucleic acids, polymerase, beads, templates, primers and salts.

EXAMPLE 10

A method for combining mixing reagents wherein two or more droplets are merged by virtue of timing their formation.

EXAMPLE 11

A commercially available emulsion PCR reagent kit is supplied with a protocol that is optimized for 10 micrometer diameter (523 femtoliter) droplets. The kit contains all the reagents necessary to perform an emulsion PCR reaction and the protocol is includes a process flow chart that describes each sample processing step. One step in the protocol calls for an aqueous mixture of reagents to be emulsified in a carrier fluid. Since the protocol is optimized for 10 micrometer droplets, an emulsifier unit comprising one embodiment of the present invention is selected for use. The unit is loaded with the reagents as specified in the PCR protocol and is set up to produce 10 micrometer droplets. The unit produces the emulsion.

EXAMPLE 12

An emulsion PCR kit protocol requires that two types of microdroplet emulsions are formed separately and then combined. Three fluid reagents are loaded into an emulsifier unit comprising one embodiment of the present invention. The fluids are a first aqueous fluid, a second aqueous fluid, and a third non-aqueous carrier fluid. Each of the aqueous fluids are directed through one or more separate fluid gap junctions and combined with the carrier fluid to create two separate emulsion droplet streams. The two droplet streams are directed toward each other such that the droplets are caused to me before exiting the emulsifier unit.

EXAMPLE 13

In one embodiment of a device as in Example 1, the microfluidic path diameters and junction gaps are sized such that they are capable of producing droplets with a mean volume between 1-100 picoliters. In another embodiment of the device as in Example 1, the microfluidic path diameters and junction gaps are sized such that they are capable of producing droplets with a mean volume between 50-5000 femtoliters. In yet another embodiment of the device the microfluidic pathways and junction gaps are sized such that they are capable of producing droplets with a mean diameter between 300-700 femtoliters.

It will be appreciated that the dimensions of microfluidic channels and the inter-channel gap junctions are exceedingly small. Non-limiting examples include: microfluidic channels: 1-100 μm (with midrange dimensions being preferred) inter-channel gap junctions: the same size as, or slightly smaller than, the transverse channels. Smaller microfluidic channels and larger inter-channel gaps permit smaller droplets to be obtained. Smaller inter-channel gaps require less carrier fluid in the system, yielding a higher reagent, concentration in the final composition. Smaller microfluidic channel dimensions permit smaller droplets to be generated, which should yield a greater number of droplets in the final composition per unit volume, e.g., more droplets per mL.

In a preferred embodiment of the invention, the product is comprised just two plastic parts and a single short, segment of capillary tube. The first, manufacturing step of the disposable device begins with a round glass capillary tube. Inexpensive and uniform, glass capillary tubes with the desirable inner and outer diameters are first cut into short segments. Capillary tube segments are then inserted into molded polycarbonate parts comprised of the upper fluid chamber and a base. Capillary tubes are then sealed into position with a heated press to form the inner subassembly, which acts as a captive fixture for the manufacturing process that will remain with the part.

Forming the microfluidic gap is the second manufacturing step in this preferred example. After aligning the part using the inner subassembly as a fixturing tool, a laser is used to cut a clean line through the capillary tube perpendicular to the central axis of the capillary tube. In general, a narrow beam is preferred, and a second parallel cut is made to create the desired gap. Some polycarbonate material may be removed or melted by the laser beam, but the inner subassembly has been designed to retain its strength and dimensional stability during the laser cutting process.

In some embodiments, where heat-sensitive compounds are present, it is contemplated that the apparatus will be operated above or below room temperature (~25° C.), in the range of 30 to 200° F. (−1 to 92° C.), with 30 to 80° F. (1 to 100° C.) being most desirable for most PCR droplet chemistry. In other embodiments, where more thermally stable materials are employed, e.g., where the droplets being formed are solid organic polymer beads, or where the apparatus may be operated at, even higher temperatures, e.g., 300° F. (147° C.). Accordingly, it is contemplated that the apparatus will be operated at a temperature of from 20 to 300° F. (−7 to 147° C. or, alternatively, 20 to 200° F. (−7 to 92° C.), or alternatively, 20 to 100° F. (−7 to 37° C.).

It is also contemplated that the pressures of the first and second liquids in the apparatus is carefully controlled. In one embodiment, each of the liquids has, independently, a pressure of 2000 psi or less, e.g., from 10-100 psi; more typically 20-100 psi (excluding the pervaporation unit, which, in one embodiment, is expected to operate at a higher pressure). In another embodiment, either or both liquids have a pressure that exceeds 100 psi. The two liquids can be supplied by a pressure supply system, which is coupled to the fluid gap junctions and the inlet port of the inlet/outlet manifold.

In another embodiment the device is formed as follows: Two lengths of round capillary tubing with inner diameters in the range of 1-1000 micrometers arranged axially and affixed to a substrate such that their opposing flat ends maintain a uniform surface-to-surface gap of between 1-1000 micrometers to form an assembly, with the open central microfluidic channel likewise centered axially with respect to each other, and furthermore with the distal end of one capillary tube in fluid communication with a first fluid chamber, and the space between the tubes forming a microfluidic gap junction in fluid communication with a second fluid chamber, and the two fluid chambers in fluid communication with each other such that when fluids are pressurized, the gap junction forms droplets.

Embodiments encompass an apparatus for preparing an emulsion of substantially uniform droplets, the apparatus having a first fluid chamber, a second fluid chamber, an inlet, an outlet, and at least one microfluidic channel having a first distal end and a second distal end that is dimensionally defined by the solid material in which it is formed and connects the first fluid chamber to the outlet, where the microfluidic channel is divided along a plane that is perpendicular to the central axis of the microfluidic channel, and a division of the at least one microfluidic channel spans a gap that is less than one millimeter when measured from the surface of the first distal end to the second distal end, the gap being in fluid communication with the second fluid chamber to form a fluid junction. In an apparatus embodiment, the solid material comprising the capillary body is notched or partially cut, but not fully divided, such that, the microfluidic channel is breached but that at least a portion of the tube body remains axially intact. A method of making substantially uniformly sized droplets includes forming droplets of a first liquid in a laminar flow of a second liquid, each droplet having a mean droplet volume of between 1 nL and 1 fL and forming droplets by moving the first liquid from a first fluid chamber through a microfluidic channel and across an open gap in said microfluidic channel that is in fluid communication with a second fluid chamber containing a second liquid, wherein the first and second liquids are no more than sparingly soluble in one another. In an apparatus embodiment, the ratio of the fluid gap distance to the mean diameter of the microfluidic channel is between 1/30 and 30. In an apparatus embodiment, the ratio of the fluid gap distance to the mean diameter of the microfluidic channel is between 1/3 and 3. In a method embodiment, one fluid gap junction generates >1,000 per second.

What is claimed is:

1. A system for forming emulsion droplets, said system comprising:
    a body having an inlet port, an outlet, and a reservoir configured to receive both an aqueous phase and an organic phase through the inlet port, wherein the reservoir has a top portion and a bottom portion;
    a barrier within the body, wherein the barrier is configured to restrict flow of the aqueous phase from the top portion of the reservoir to the bottom portion of the reservoir and allow flow of the organic phase from the top portion of the reservoir to the bottom portion of the reservoir; and
    a tubular structure within the body providing fluidic communication between the top portion of the reservoir and the outlet,
    wherein the tubular structure has a lumen aligned with a vertical axis of the body and a slot intersecting the lumen,
    wherein the slot is located within the bottom portion the reservoir,
    wherein the barrier is disposed between the top portion of the reservoir and the slot of the tubular structure,
    wherein the lumen is configured to create a first fluidic pathway of the aqueous phase flowing from the top portion of the reservoir toward the slot, the slot is configured to create a second fluidic pathway of the organic phase flowing from the bottom portion of the reservoir to the lumen, the first fluidic pathway and the second fluidic pathway intersecting at a junction, so as to form emulsion droplets of the aqueous phase at or downstream of the junction in a third fluidic pathway upon application of a pressure differential between the reservoir and the outlet,
    wherein the emulsion droplets in the third fluidic pathway flow through the lumen downstream of the first and second fluidic pathways and are dispensed through the outlet, and
    wherein (i) the barrier comprises a conical element with at least two fins which are spaced to divert flow of the aqueous phase to the first fluidic pathway while allowing flow of the organic phase to the second fluidic pathway, or (ii) the barrier comprises a plurality of channels or shafts that restrict flow of the aqueous phase from the top portion of the reservoir to the bottom portion of the reservoir and that allow flow of the organic phase from the top portion of the reservoir to the bottom portion of the reservoir.

2. A system as in claim 1, wherein the barrier has a hydrophobic surface.

3. A system as in claim 1, wherein the first fluidic pathway is disposed along the vertical axis of the body and the second fluidic pathway is disposed to deliver the organic phase laterally into the first fluidic pathway.

4. A system as in claim 1, wherein the body is configured to be removably placed into a single receptacle.

5. A system as in claim 4, further comprising a centrifuge comprising a rotor configured to receive a plurality of the single receptacles and to apply a radial force along axes of the plurality of the single receptacles when the rotor is spun.

6. A system as in claim 1, further comprising a differential pressure generator having at least one port connectable to the inlet and/or outlet of the reservoir.

7. A system as in claim 1, wherein the barrier and the tubular structure are removably positionable within the body.

8. A system as in claim 1, wherein the barrier and the tubular structure are integral with the body.

9. A system as in claim 1, wherein the body has a form of a well.

10. A system as in claim 1, wherein the body has a form of a microcentrifuge tube.

11. A system as in claim 1, further comprising at least one additional body, wherein each of the at least one additional body has
    a) its own inlet, its own outlet, and its own reservoir configured to receive both the aqueous phase and the organic phase through its own inlet,
    b) its own barrier configured to restrict flow of the aqueous phase from its own top portion of its own reservoir and allow flow of the organic phase from its own top portion of its own reservoir to its own bottom portion of its own reservoir, and
    c) its own tubular structure configured to combine a stream of the aqueous phase flowing from its own top portion of its own reservoir with a stream of the organic phase flowing from its own bottom portion of its own reservoir to form emulsion droplets which are dispensed through its own outlet.

12. A system as in claim 11, wherein each of the at least one additional body are arranged to correspond with a microwell plate so that each outlet is alignable with a well in the microwell plate.

13. A system as in claim 11, wherein the at least one additional body comprises 96 additional bodies that are arranged to correspond with a 96 microwell plate.

14. A system as in claim 1, wherein flow of the aqueous phase along the first fluidic pathway and flow of the organic phase along the second fluidic pathway occur by motive forces generated by the differential pressure between the reservoir and the outlet.

15. A system as in claim 14, further comprising at least one compressed gas, a vacuum pump, a piston, and/or a centrifuge which influence the motive forces.

16. A system as in claim 1, wherein the barrier comprises the plurality of channels or shafts that restrict flow of the aqueous phase from the top portion of the reservoir to the bottom portion of the reservoir and that allow flow of the organic phase from the top portion of the reservoir to the bottom portion of the reservoir, and wherein the barrier has a conical shape configured to direct the aqueous phase toward the tubular structure.

17. A system as in claim 1, wherein the tubular structure combines the first fluidic pathway of the aqueous phase flowing from the top portion of the reservoir in a coaxial arrangement with the second fluidic pathway of the organic phase flowing from the bottom portion of the reservoir.

18. A system as in claim 1, wherein the slot comprises a partial through cut of the tubular structure.

19. A system as in claim 1, wherein the body is configured to mate with a microwell receptacle plate so that the microwell receptacle plate receives the emulsion droplets in an individually isolated collection well.

20. A system as in claim 1, wherein the emulsion droplets are formed with a coefficient of variation of less than 50%.

21. A system as in claim 20 wherein the emulsion droplets are formed with a coefficient of variation of less than 30%.

22. A system as in claim 21, wherein the emulsion droplets are formed with a coefficient of variation of less than 10%.

23. A system as in claim 1, wherein the barrier is arranged within the body so that gravity acts to draw the aqueous phase and the organic phase downward toward the barrier.

24. A system as in claim 23, wherein the tubular structure is arranged so that the aqueous phase passes through the tubular structure to form the first fluidic pathway of the aqueous phase.

25. A system as in claim 24, wherein the tubular structure is arranged so that a distal end of the tubular structure is flush with a bottom surface of the reservoir.

26. A system as in claim 1, wherein the reservoir receptacle is preloaded with the aqueous phase.

27. A system as in claim 26, wherein the aqueous phase comprises nucleic acids.

28. A system as in claim 27, wherein the nucleic acids comprise double-stranded DNA.

29. A system as in claim 1, wherein the lumen of the tubular structure has an inner diameter, wherein the slot has a height, and wherein the inner diameter of the lumen and the height of the slot are equal.

30. A system as in claim 1, wherein the lumen has an inner diameter having a value within a range from 1 micrometer to 1000 micrometers.

31. A system as in claim 1, wherein the lumen has an inner diameter having a value within a range from 1 micrometer to 1000 micrometers and the slot has a height having a value within a range from 1 micrometer to 1000 micrometers.

32. A system as in claim 1, wherein the slot has a height and the lumen has an inner diameter, and wherein a ratio of the height to the inner diameter has a value within a range from 1:3 to 3:1.

33. A system as in claim 1, wherein the slot has a height and the lumen has an inner diameter, and wherein a ratio of the height to the inner diameter has a value within a range from 1:30 to 30:1.

34. A system as in claim 1, wherein the barrier comprises the conical element with at least two fins which are spaced to divert flow of the aqueous phase to the first fluidic pathway while allowing flow of the organic phase to the second fluidic pathway.

35. A system as in claim 1, wherein the barrier comprises the plurality of channels or shafts that restrict flow of the aqueous phase from the top portion of the reservoir to the bottom portion of the reservoir and that allow flow of the organic phase from the top portion of the reservoir to the bottom portion of the reservoir.

36. A system as in claim 35, wherein the barrier comprises the plurality of channels that restrict flow of the aqueous phase from the top portion of the reservoir to the bottom portion of the reservoir and that allow flow of the organic phase from the top portion of the reservoir to the bottom portion of the reservoir.

37. A system as in claim 35, wherein the barrier comprises the plurality of shafts that restrict flow of the aqueous phase from the top portion of the reservoir to the bottom portion of the reservoir and that allow flow of the organic phase from the top portion of the reservoir to the bottom portion of the reservoir.

* * * * *